US006888131B2

(12) United States Patent
Berlin

(10) Patent No.: US 6,888,131 B2
(45) Date of Patent: May 3, 2005

(54) SAMPLE SUPPORT FOR MASS SPECTROMETERS

(75) Inventor: Kurt Berlin, Stahnsdorf (DE)

(73) Assignee: Epigenomics AG, Berlin (DE)

( * ) Notice: Subject to any disclaimer, the term of this patent is extended or adjusted under 35 U.S.C. 154(b) by 0 days.

(21) Appl. No.: 10/296,490

(22) PCT Filed: May 23, 2001

(86) PCT No.: PCT/DE01/02079

§ 371 (c)(1), (2), (4) Date: Nov. 25, 2002

(87) PCT Pub. No.: WO01/91154

PCT Pub. Date: Nov. 29, 2001

(65) Prior Publication Data

US 2004/0113066 A1 Jun. 17, 2004

(30) Foreign Application Priority Data

May 23, 2000 (DE) ........................................ 100 27 120

(51) Int. Cl.[7] ........................... H01J 49/04; H05B 3/06; C12Q 1/16; C12Q 1/68

(52) U.S. Cl. ................... 250/288; 250/287; 250/440.11

(58) Field of Search ................................ 250/288, 287, 250/440.11, 289, 424, 423 R, 442.11, 281, 282; 435/89, 91.1, 91.3, 287.1, 287.2, 287.3, 288.3, 288.4; 436/46, 47, 94, 173

(56) References Cited

U.S. PATENT DOCUMENTS

| | | | | | |
|---|---|---|---|---|---|
| 3,096,435 | A | | 7/1963 | Burdg | |
| 3,886,358 | A | | 5/1975 | McLaughlin et al. | |
| 4,384,193 | A | * | 5/1983 | Kledzik et al. | 219/521 |
| 5,498,545 | A | * | 3/1996 | Vestal | 436/47 |
| 5,770,860 | A | * | 6/1998 | Franzen | 250/288 |
| 5,994,065 | A | | 11/1999 | Van Ness | |
| 6,043,031 | A | * | 3/2000 | Koster et al. | 435/6 |
| 6,175,112 | B1 | * | 1/2001 | Karger et al. | 250/288 |
| 6,465,778 | B1 | | 10/2002 | Koster et al. | |
| 2002/0094533 | A1 | * | 7/2002 | Hess et al. | 435/6 |
| 2003/0124716 | A1 | * | 7/2003 | Hess et al. | 435/287.1 |
| 2003/0180807 | A1 | * | 9/2003 | Hess et al. | 435/7.1 |
| 2004/0113066 | A1 | * | 6/2004 | Berlin | 250/288 |

FOREIGN PATENT DOCUMENTS

| | | |
|---|---|---|
| DE | 197 12 195 | 9/1998 |
| EP | 964 427 | 12/1999 |
| GB | 2 156 073 | 10/1985 |
| GB | 2 178 534 | 2/1987 |
| WO | WO 99/00657 | 1/1999 |
| WO | WO 99/29898 | 6/1999 |
| WO | WO 00/67293 | 11/2000 |
| WO | WO 01/90761 | 11/2001 |

OTHER PUBLICATIONS

"A structure for Deoxyribose Nucleic Acid", website article dated Apr. 25, 1953, downloaded from http://biocrs.biomed.brown.edu/Books/Chapters/Ch_8/DH–Paper.html.*

* cited by examiner

*Primary Examiner*—John R. Lee
*Assistant Examiner*—Bernard E. Souw
(74) *Attorney, Agent, or Firm*—Kriegsman & Kriegsman

(57) ABSTRACT

A sample holder is described, which is loaded with metal or glass slides. This arrangement serves for the analysis of DNA arrays in the MALDI-TOF mass spectrometer.

6 Claims, 1 Drawing Sheet

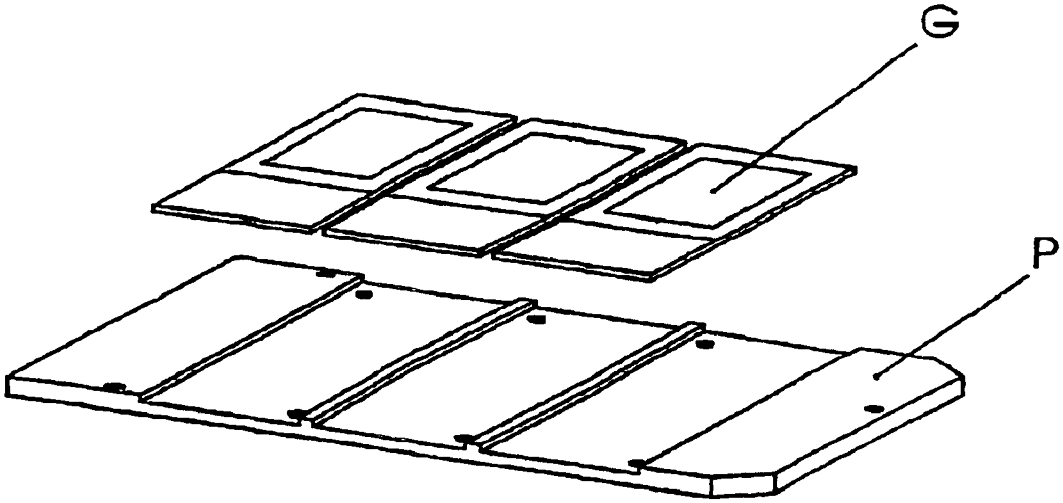
G
P

SAMPLE SUPPORT FOR MASS SPECTROMETERS

The present invention describes a sample holder for the mass spectrometer, particularly for the MALDI-TOF mass spectrometer.

Matrix-assisted laser desorption/ionization time-of flight mass spectrometry (MALDI-TOF) has revolutionized the analysis of biomolecules (Karas, M. & Hillenkamp, F. Anal. Chem. 60, 2299-2301 (1988)).

A number of sample holders are known in the prior art, which are also suitable for MALDI-TOF mass spectrometry. Thus, U.S. Pat. No. 4,384,193 describes a sample-holder device, which is suitable for receiving microscope slides and is used for the incubation of samples. MALDI-TOF mass spectrometry, however, was as yet unknown at the time point of publication of this document. EP-A 0 964,427 describes holders for MALDI-TOF mass spectrometry in a general manner. However, the holders must be configured so that they are always conductive for the analyte. It is known from DE-A 197 12195 and U.S. Pat. No. 5,770,860 that microtiter plates can also be used for MALDI-TOF mass spectrometry. DE-A 198 34070 finally discloses that sample holders for MALDI-TOF mass spectrometry could also be produced from hydrophobic material, but that care must always be taken that the surface is electrically conducting (for example, by filling with graphite).

The sample holders usually used for MALDI-TOF mass spectrometry are made of metal and are designed for individual samples, often 26 or 100 samples, or more recently also for 384 samples, and are usually of a type such that the sample, together with a matrix, for the most part of an organic acid, is introduced directly onto its position on the sample holder. These are essentially planar metal plates. The sample holders with 384 sample positions, which were recently introduced on the market by the Bruker company, correspond in their grid structure and dimensions to a microtiter plate. These sample holders are not suitable for the direct use of biochips (oligomer arrays) in the mass spectrometer, since it is necessary to immobilize oligonucleotides, which can be done only with great expense on a sample holder.

Sample holders that are used for immobilizing [oligonucleotides] on a surface possess a metal surface that has been chemically modified or coated with glass (WO 99/29898). The disadvantage of these surfaces is that the coating is not particularly uniform for highly sensitive analysis. Furthermore, the coating process is usually either very laborious and/or cost-intensive. Metal holders with glass coating are known, but serve rather to create a particularly smooth surface in order to solve critical calibration problems.

Biochips, in contrast, are frequently used in microscope-slide format. A few chemical modification steps suffice for the most part to activate the glass surface of a conventional microscope slide as is used for microscopy, so that preferably a covalent chemical bond is possible for the probe nucleotides that are introduced and which lie in a pregiven grid pattern on the surface of the microscope slide An overview of the state of the art in oligomer array production can be taken also from a special issue of Nature Genetics which appeared in January 1999 (Nature Genetics Supplement, Volume 21, January 1999), the literature cited therein, and U.S. Pat. No. 5,994,065 on methods for the production of solid supports for target molecules such as oligonucleotides with reduced nonspecific background signal.

The technical problem that is the basis for the present invention was thus the circumstance that there was no technological compatability relative to material and form for the use of biochips in the mass spectrometer.

The object of the present invention is to create a sample holder which overcomes the disadvantages of the prior art.

The subject of the invention is a sample holder which permits the introduction of conventional biochips in microscope-slide format in a commercial MALDI mass spectrometer.

The object of the invention is solved by creating a sample holder for the mass spectrometer, particularly for the MALDI-TOF mass spectrometer, comprised of metal or another conductive material, which is characterized in that this sample holder has at least one recess for the uptake of holders for biological samples.

According to the invention, it is preferred that the recesses correspond in their dimensions to conventional microscope slides. It is particularly preferred that the dimensions are as follows: between 75 and 130 mm in length, between 25 and 100 mm in width and between 2 and 20 mm in height.

A sample holder is preferred according to the invention, wherein at least one holder for biological samples is arranged thereon. It is preferred that the holders for biological samples correspond to conventional microscope slides. It is further preferred that the dimensions of the holders for biological samples are between 72 and 78 mm in length, 22 to 28 mm in width and 0.5 to 2 mm in height. It is also preferred that the holders for biological samples are comprised of metal.

It is highly preferred that the holder for biological samples is comprised of a nonconducting material and/or glass.

It is most particularly preferred that DNA fragments or oligonucleotides are introduced in a rectangular or hexagonal pattern on the holder for biological samples.

According to the invention, it is further provided that the sample holder and the holder for biological samples are attached together by means of double-sided adhesive tape, screws, springs, snap closures, wire clips and/or tracks.

It is also preferred that the sample holder according to the invention corresponds in format to a microtiter plate. A sample holder with dimensions of roughly 123 mm×82 mm×9.5 mm is particularly preferred.

Another subject of the present invention is the use of a sample holder according to one of the preceding claims* for the analysis of polymorphisms and/or DNA methylation in DNA samples.

* sic—Trans. Note.

The present invention thus describes a sample holder for the MALDI mass spectrometer. This sample holder is comprised of an electrically conducting material, preferably steel or aluminum. Recesses, which serve for the uptake of plates which can be either also of metal or of glass or silicon are found in the sample holder. The invention is also based on the surprising knowledge that conventional microscope slides can be introduced into such a mass spectrometer without the lack of conductivity of the glass holder adversely affecting the measurement result. The samples are found on the plates which can be utilized in the sample holder.

According to the invention, sample holders are thus particularly preferred on which holders for biological samples are introduced or attached, which comprise non-metallic and/or non-conducting materials. Most particularly preferred are holders for biological samples that are made of glass.

A sample holder for a MALDI-TOF spectrometer, preferably comprised of metal, is described, which has recesses for the uptake of 1–5 plates, which preferably correspond in their dimensions to conventional microscope slides. Preferably, the dimensions of the sample holder are as follows: between 75 and 130 mm in length, between 25 and 100 mm in width and between 2 and 20 mm in height. The dimensions of the plates, which may be comprised of glass, silicon, or metal, are, particularly preferred, 72–78 mm×22–28 mm×0.5–2 mm. The latter correspond to the dimensions of conventional microscope slides, whose precise dimensions are variable in an international comparison.

In a preferred variant, the plates are attached to the sample holder with double-sided adhesive tape. In another particularly preferred variant, the attachment is made with screws, springs, snap closures, wire clips, or tracks.

The sample holder is preferably used for matrix-assisted laser desorption/ionization mass spectrometry (MALDI-TOF), which works with 384 defined positions per sample holder and thus corresponds to a sample holder in the format of a microtiter plate (approximately 123 mm×82 mm×9.5 mm).

The plates, which preferably function as biochips (oligomer arrays) and thus hold immobilized oligonucleotides, can also be used separately from the sample holder, for example, in hybridization experiments, as they are the state of the art for oligomer arrays. A treatment of the surface of the sample holder, properly speaking, which only receives the plates, is dispensed with. Hybridization products need no longer be transferred onto the sample holder, but can be investigated directly on the pre-given surface of the plates used.

The DNA fragments or oligonucleotides, which are preferably introduced onto the surface, are arranged in a rectangular or hexagonal pattern.

The time-consuming coating of the surfaces is dispensed with, since the cost-favorable glass holders have the same function with a more uniform surface. Coated glasses of the type required for the present invention, as opposed to coated metal holders, can be obtained commercially, which represents another essential advantage.

The present invention thus provides an apparatus-type linking component between the preparation of the oligomer array, for example, and its measurement and evaluation in mass spectrometers. The time-consuming transfer of samples is avoided in this way. The sample holder according to the invention thus represents an essential facilitation of labor and an immense cost savings. A particular advantage is also that conventional microscope slides and/or sample holders can be used. Such conventional holders are also suitable for automated analysis. Another cost advantage thus results from this. Analyses can thus be rapidly performed in a cost-favorable manner with a high throughput. The sample holder according to the invention thus combines the field of sample preparation and that of measurement of samples in an astonishingly simple way.

The subject of the present invention and a particularly preferred form of embodiment is a sample holder according to the invention for the mass spectrometer, particularly for the MALDI-TOF mass spectrometer, which is comprised of metal or another conductive material, whereby this sample holder has at least one recess for the uptake of holders for biological samples as well as at least one holder for biological samples arranged thereon, and is characterized in that the holders for biological samples are comprised of non-conducting material and/or of glass. It is further preferred that the holders for biological samples are comprised of non-conducting material and/or of glass.

Preferably, the sample holder is used for the analysis of polymorphisms and/or DNA methylation in DNA samples.

A preferred form of embodiment of the sample holder according to the invention is shown in FIG. 1. The sample holder P according to the invention which is comprised of metal or another conductive material for the MALDI-TOF device (BIFLEX III BT 1903, Bruker Analytical Systems) can preferably be loaded with 1 to 3 glass slides G. These have a size of 76 mm×25 mm×1 mm.

What is claimed is:

1. A sample holder for use in a mass spectrometer, particularly a MALDI-TOF mass spectrometer, said sample holder comprising metal or another conductive material, wherein this sample holder has at least one recess dimensioned for the uptake of one or more biochips in microscope-slide format, the sample holder and the one or more biochips being attached together by at least one attaching device selected from the group consisting of double-sided adhesive tape, screws, springs, snap closures, wire clips and tracks, said biochips comprising at least one of a non-conducting material and glass.

2. The sample holder according to claim 1, further characterized in that the dimensions of the biochips are between 72 and 78 mm in length, 22 to 28 mm in width and 0.5 to 2 mm in height.

3. The sample holder according to claim 1, further characterized in that DNA fragments or oligonucleotides are introduced in a rectangular or hexagonal pattern on the biochips.

4. The sample holder according to claim 1, further characterized in that this holder corresponds in format to a microtiter plate.

5. The sample holder according to claim 4, in dimensions of approximately 123 mm ×82 mm×9.5 mm.

6. Use of a sample holder according to any one of the preceding claims for the analysis of polymorphisms and/or DNA methylation in DNA samples.

* * * * *